United States Patent [19]

Hähn et al.

[11] Patent Number: 5,450,817
[45] Date of Patent: Sep. 19, 1995

[54] PROCESS FOR PRODUCTION OF SORBENTS FOR UPTAKE OF LIQUIDS

[75] Inventors: Reinhard Hähn, Landshut; Norbert Schall, Langenpreising; Rolf Ahlers, Landshut; Otto Haubensak, Brannenburg; Max Eisgruber, Bruckberg, all of Germany

[73] Assignee: Sud-Chemie AG, Munich, Germany

[21] Appl. No.: 170,037

[22] Filed: Dec. 20, 1993

[30] Foreign Application Priority Data

Dec. 21, 1992 [DE] Germany .......... 42 43 389.4

[51] Int. Cl.$^6$ .............................................. A01K 1/015
[52] U.S. Cl. .................................................. 119/173
[58] Field of Search ........................ 119/171, 172, 173

[56] References Cited

U.S. PATENT DOCUMENTS

| | | |
|---|---|---|
| Re. 33,983 | 7/1992 | Hughes . |
| 3,240,616 | 3/1966 | Harasowski et al. . |
| 3,408,350 | 10/1968 | Torok et al. . |
| 4,591,581 | 5/1986 | Crampton et al. ............... 502/407 |
| 4,641,605 | 2/1987 | Gordon . |
| 4,657,881 | 4/1987 | Crampton et al. ............... 502/80 |
| 4,865,761 | 9/1989 | Mandel et al. ............... 252/190 |
| 4,913,835 | 4/1990 | Mandel et al. . |
| 4,914,066 | 4/1990 | Woodrum ............... 502/62 |
| 4,949,672 | 8/1990 | Ratcliff et al. . |
| 5,000,115 | 3/1991 | Hughes . |
| 5,037,412 | 8/1991 | Tanzer et al. . |
| 5,129,365 | 7/1992 | Hughes . |
| 5,161,686 | 11/1992 | Weber et al. . |
| 5,176,108 | 1/1993 | Jenkins et al. . |
| 5,295,456 | 3/1994 | Lawson ............... 119/172 |
| 5,303,676 | 4/1994 | Lawson ............... 119/173 |

*Primary Examiner*—Gene Mancene
*Assistant Examiner*—Thomas Price
*Attorney, Agent, or Firm*—Scott R. Cox

[57] ABSTRACT

A process for the production of sorbents based on bentonite for the uptake of liquids is described. The process is characterized in that a poorly swelling bentonite with a water uptake capacity of less than 100% (in terms of the dried bentonite with a residual water content of 6 wt. %), a montmorillonite content of around 40–65 wt. % and a water content of 20–40 wt. % is homogenized with a basic-reacting alkaline metal compound by thorough kneading and converted by ion exchange to a swelling bentonite, while the pH value of the mixture is not more than 10.5, the mixture is gently dried, and the dried mixture is fragmented.

18 Claims, No Drawings

PROCESS FOR PRODUCTION OF SORBENTS FOR UPTAKE OF LIQUIDS

BACKGROUND OF THE INVENTION

The invention is directed to a process for production of sorbents for uptake of liquids. These sorbents are suitable for taking up any desired liquids; however, they are especially good as pet litter.

The keeping of pets in a largely urbanized environment is increasingly dependent on the use of litter materials. The task of these materials is to absorb the fluids given off by the animals and to suppress or prevent the development of odor if possible. Moreover, they are required to remove moisture from the semisolid, moist animal excrement and excretions, in order to reduce the development of odor. Good litter materials, furthermore, have the property of taking up the excreted or removed fluids by forming a compact clump, which can be removed in a simple and economical way. Therefore, an optimal animal litter has a high absorption capacity.

The products that can be found on the market include organic substances such as straw, sawdust, wood shavings, bark, porous synthetic beads, shredded paper, cellulose fibers, agricultural wastes, polyacrylates, etc. These are used by themselves or in mixtures with inorganic materials. The disadvantage of the organic litter materials is an often unsatisfactory clumping or consistency of the clump, as well as their tendency to bacterial decomposition, especially in conjunction with moisture.

Japanese No. 60,258,101 discloses water dispersable granulates used as pest control agents containing a mixture of bentonite and diatomaceous earth as the carrier, as well as a small quantity of alkaline phosphate. These products are only mixtures of materials. There is no activation of the bentonite.

Japanese No. 58,128,146 discloses a sorbent for volatile inorganic hydrides which are obtained by the impregnation of solid silicate carriers, such as diatomaceous earth, calcium silicate or bentonite, with aqueous solutions of alkalis such as sodium hydroxide, potassium hydroxide or calcium hydroxide. There is no kneading or activation of the sorbent disclosed.

Japanese No. 53,065,283 discloses a method for removing contaminants from exhaust gases by the use of granulates of bentonite, potassium permanganate, sodium hydroxide, cement as a binding agent and, possibly, activated charcoal. The sodium hydroxide is not kneaded with the bentonite nor is it used for its activation.

Japanese No. 52,065,767 discloses a method for the removal of ammonium compounds, in which the ammonium compound is brought into contact with the synthetic aluminum silicate or a clay material, such as bentonite, which has previously been made amorphous. The absorbent after its use is regenerated by a treatment with an alkaline solution, whereupon the bound ammonium ions are replaced by alkaline ions.

U.S. Pat. No. 5,037,412 discloses a sorption pad for body fluid containing a sorbent such as a mixture of citric acid, sodium biocarbonate and zeolite in a casing. Bentonite is not disclosed in this patent.

U.S. Pat. No. 4,641,605 discloses an animal litter which delays the release of ammonia. The litter contains a sorbent, such as bentonite, which is mixed with oxidation agents, such as alkaline persulfates and ammonium persulfate. Neither serves as an activation agent for the product.

U.S. Pat. No. 4,913,835 discloses an agent for the neutralization and solidification of spilled, hazardous alkaline liquids comprised of a mixture of weak organic acids, a clay mineral and a water soluble, slightly acid salt. Once again, no activation of the clay mineral is disclosed.

U.S. Pat. Nos. 4,949,672 and 5,176,108 disclose litter materials based on bentonite, which are impregnated with a liquid carrier containing a bactericidal boron compound and an alkaline hydroxide. No activation of the bentonite by kneading is described.

There are also bentonite-based litter materials, as disclosed in U.S. Pat. Nos. 5,000,115, 4,657,881 and 5,000,115, for example, which have certain advantages over the organic litters. Through their ability to swell with aqueous liquids, the bentonites are capable of forming clumps. Because of this clumping, the portion of the litter wetted by the fluid can be removed separately, thus economizing on litter. The special structure of the bentonites is also responsible for their ability to adsorb unpleasant odors produced by the animal's excretions and excrement. Disposal of bentonites, furthermore, is not a burden on the environment.

According to the above-mentioned state of the art, sodium bentonites or mixtures of sodium bentonites and calcium bentonites are used as sorbents, e.g., litter material for pets. These sorbents can be used in granulated form.

However, sodium bentonites are only available in certain regions and for this reason they are usually employed only for special applications, e.g., as binder for foundry mold sand and as thickening and thixotropic agent for aqueous media. High-quality calcium bentonites can be activated for these purposes, although large quantities of alkaline activation agents (e.g., at least 3.5% sodium carbonate, in terms of the dry clay) are required in order to achieve the requisite binding ability. On the other hand, there are large quantities of calcium bentonites which are not suitable for these special applications, even after an alkaline activation, due to the low content of the primary mineral - montmorillonite.

Therefore an object of the invention is to supply these formerly unusable bentonites with low montmorillonite content, occasionally thrown away as wastes, for an economic and ecologically meaningful usage.

SUMMARY OF THE INVENTION

The invention is directed to bentonite-based sorbents for the uptake of liquids produced by the process of (1) homogenizing a poorly swelling bentonite with a water uptake capacity of less than 110%, preferably less than 115% (in terms of the dried bentonite with a residual water content of 6 wt. %), a montmorillonite content of around 40-65 wt. %, preferably 50-60 wt. %, and a water content of 20-40 wt. %, preferably 25-35 wt. %, with a basic-reacting alkaline metal compound by thoroughly kneading thus converting poorly swelling bentonite by ion exchange to a swelling bentonite, while the pH value of the mixture is not more than 10.5, preferably not more than 10.0 to form a mixture, (2) drying the mixture and (3) fragmenting the dried mixture.

The water content, the water uptake capacity, and the pH value are determined by the methods given below.

The poorly swelling bentonites used as the starting material have not heretofore permitted any meaningful usage and had to be thrown away. The poor swelling ability is primarily caused by the fact that these bentonites contain nonswelling components such as quartz, kaolin, mica, feldspar, calcite and dolomite. Furthermore, however, the poor swelling ability is also caused by the fact that the montmorillonite is primarily present in the form of calcium montmorillonite. When the bentonite is kneaded with the basic-reacting alkaline metal compound, the calcium ions in the interlayers of the montmorillonite are primarily replaced by alkaline ions, chiefly sodium ions. The energy consumption of the kneading is generally 2–10, preferably 3–6 kWh/ton of kneaded mixture.

The ion exchange greatly improves the swelling capacity and, thus, the water uptake capacity of the bentonite, so that after drying it is capable of taking up large quantities of liquid. The drying of the alkalinized bentonite is done gently, without destructive influence on the water uptake capacity of the bentonite. These conditions can be produced if the material is not exposed to more than 150° C., preferably not more than 120° C., and the residual water content does not drop below 4 wt. %, preferably not below 6 wt. %.

The dried mixture is generally present in the form of large pieces, which are fragmented in conventional manner. The fines produced by the fragmentation are usually sifted off and returned to the kneading layout.

DESCRIPTION OF THE INVENTION

The invention is directed to the use of the above-mentioned sorbent as a means of soaking up liquids, such as body fluids, oil, liquid chemicals, and as litter for pets, especially cats.

In general, one starts with an alkaline earth bentonite, especially calcium bentonite, which in its dry state has a water uptake capacity of at least 60% (in terms of crude dry clay with a residual moisture content of 6 wt. %).

As the basic-reacting alkaline metal compounds, one preferably uses the water soluble sodium salts of weak to medium strong acids, such as carbonic acid, silicic acid, oxalic acid, citric acid, phosphoric acid, or acetic acid.

Preferably, the basic-reacting alkaline metal compound (preferably, the corresponding sodium compound) is used in a quantity of 0.1 to 1.5%, preferably 0.25 to 1.5%, in terms of the dried crude bentonite (atro=absolutely dry).

Surprisingly, it has been found that even these small admixtures are capable of significantly increasing the water uptake ability of the thus treated bentonite. Larger admixtures, such as may be employed in the activation of foundry bentonite, are not useful, since they only increase the pH value of the material, which is unfavorable for its use as pet litter, since unpleasant smells may be created in this way.

In order to achieve the most intense possible ion exchange, one will preferably proceed by kneading the basic-reacting alkaline metal compound in solid form or in the form of aqueous solutions into the bentonite. This treatment can be done at room temperature, but it can be accelerated by raising the temperature.

The water uptake capacity of the untreated material, which is usually under 115%, can be more than doubled by the treatment of the invention. Through the choice of suitable alkaline metal compounds and varying the anions contained in them, it is possible to control the basic properties or the pH value of the treated material, in addition to boosting its water uptake capacity by activation. Furthermore, this activation achieves an improvement in the clumping ability and a better consistency of the clumps of liquid-saturated material by optimization of the swelling behavior.

A further optimization of the liquid uptake can be achieved by processing the dried product to a grain size of around 0.1–10 mm, preferably 1–5 mm.

Moreover, the subject of the invention is a sorbent that can be produced by the above-described process and that is characterized by a water content of roughly 3–12, preferably 4–10%, a water uptake capacity of more than 120%, preferably more than 150% (in terms of the material dried to a residual moisture content of 6 wt. %), and a pH value (measured in an 8% aqueous suspension) of 7.5–10.5, preferably 8.0–10.

Moreover, the sorbent of the invention can be blended with familiar sorbents, e.g., the above-mentioned organic sorbents. Furthermore, the sorbent may contain white pigments, disinfectant, and/or animal acceptance agents.

EXAMPLES

The following Examples describe the process for the production and use of the sorbents according to the invention:
Test Procedures The water content of the invented sorbent is determined as follows:

10 g of sorbent are exactly weighed out to 0.01 g in a shallow dish and dried to constant weight in a drying cabinet at 110° C. (at least two hours). Next, the specimen is cooled down to room temperature in a desiccator and weighed:
Evaluation:

(First weighing/Final weighing)/First weighing
×100 =water content (%)

The water uptake ability of the invented sorbent is determined by the method of the Westinghouse Company (No. 17-A) (cf. Industrial Minerals, August 1992, page 57). In this process, the sorbent, dried to a residual water content of 6 wt. %, is weighed in (weigh-in $E=20$ g) in a conical container of fine wire fabric (mesh 60=0.25 mm, diameter 7 cm, height 7.6 cm). Next, the total weight is determined (wire fabric+weigh-in $E=E_1$ in g). The filled fabric is hung for 20 minutes in a water-filled glass tray so that the sorbent is completely submerged. After 20 minutes, the wire fabric is taken out of the water and allowed to drip for around 20 minutes. Immediately after this, the weight of the container with its contents is determined ($E_2$ in g). The evaluation is done as follows:

Water uptake in percent$=(E_2-E_1)/E \times 100$

The pH value of the invented sorbent is determined as follows:

In a beaker with 1000 ml of distilled water, 80 g of sorbent (water content 6 wt. %) are placed. After standing for one hour, this is stirred by swirling for 10 minutes. The suspension is allowed to stand for 24 hours. Around 30 seconds prior to the test, it is again stirred.

The pH meter is calibrated with two buffer solutions with pH values of 7 and 9. For this, the electrode is first placed in the solution with pH value of 7 for around 30 seconds. The electrode is taken out and rinsed with distilled water. It is then placed in the solution with pH value of 9; this is adjusted as above. The electrode is again rinsed with distilled water and placed in the bentonite suspension.

Example 1 (Comparison)

Around 2 kg of freshly excavated crude Ca-bentonite (around 30 wt. % water) with a montmorillonite content of 60 wt. %, in terms of dry mass, and a water uptake capacity of 110% (in terms of a dried material with residual water content of 6%), is intensively kneaded for 5 minutes in a kneading machine with shearing action (Werner-Pfleiderer blender). The energy consumption was 2 kWh/ton. The resulting agglomerates are dried gently at 75° C. for 4 hours and fragmented to a grain size of 1–5 mm with a water content of 6 wt. %. The water uptake capacity and the pH value of the granulates are measured in suspension by the above-described methods.

The resulting values are indicated in the following table.

Example 2

The procedure of Example 1 is repeated with addition of sodium carbonate in solid form. The added quantities correspond to 0.29%, 0.58% and 1.75% $Na_2O$ (in terms of the bentonite dry substance).

Example 3

The procedure of Example 1 is repeated with addition of sodium oxalate in solid form. The added quantities correspond to 0.23%, 0.46% and 1.39% $Na_2O$ (in terms of the bentonite dry substance).

Example 4

The procedure of Example 1 is repeated with addition of sodium citrate in solid form. The added quantities correspond to 0.13%, 0.26% and 0.78% $Na_2O$ (in terms of the bentonite dry substance).

Example 5

The procedure of Example 1 is repeated with addition of sodium acetate in solid form. The added quantities correspond to 0.19%, 0.38% and 1.14% $Na_2O$ (in terms of the bentonite dry substance).

Example 6

The procedure of Example 1 is repeated with addition of an aqueous sodium carbonate solution in solid form. The added quantities correspond to 0.29%, 0.58%, 1.16%, and 1.75% $Na_2O$ (in terms of the bentonite dry substance).

Example 7

The procedure of Example 1 is repeated with addition of an aqueous sodium oxalate solution in solid form. The added quantities correspond to 0.28%, 0.60%, 1.16%, and 1.76% $Na_2O$ (in terms of the bentonite dry substance).

Example 8

The procedure of Example 1 is repeated with addition of an aqueous sodium citrate solution in solid form. The added quantities correspond to 0.29%, 0.60%, and 1.17% $Na_2O$ (in terms of the bentonite dry substance).

Example 9

The procedure of Example 1 is repeated with addition of a water glass solution. The added quantities correspond to an $Na_2O$ content of 0.5%, 1.0% and 1.5%.

TABLE

| Example | Bentonite Activation | Added Quantity Computed as $Na_2O$ (%) | Water Uptake Capacity (%) | pH Value |
|---|---|---|---|---|
| 1 | no additive |  | 110 | 8.6 |
| 2 | Na-carbonate | 0.29 | 150 | 9.3 |
|  | (in solid | 0.58 | 210 | 9.7 |
|  | form) | 1.75 | 250 | 10.5 |
| 3 | Na-oxalate (in | 0.23 | 130 | 8.6 |
|  | solid form) | 0.46 | 190 | 8.7 |
|  |  | 1.39 | 250 | 8.9 |
| 4 | Na-citrate (in | 0.13 | 110 | 9.0 |
|  | solid form) | 0.26 | 110 | 9.0 |
|  |  | 0.78 | 150 | 9.1 |
| 5 | Na-acetate (in | 0.19 | 140 | 9.2 |
|  | solid form) | 0.38 | 130 | 9.1 |
|  |  | 1.14 | 140 | 9.0 |
| 6 | Na-carbonate | 0.25 | 170 | 9.5 |
|  | (in dissolved | 0.58 | 190 | 9.7 |
|  | form) | 1.16 | 280 | 10.1 |
|  |  | 1.75 | 320 | 10.4 |
| 7 | Na-oxalate (in | 0.28 | 160 | 8.8 |
|  | dissolved | 0.60 | 180 | 9.0 |
|  | form) | 1.16 | 300 | 9.2 |
|  |  | 1.76 | 280 | 9.6 |
| 8 | Na-citrate (in | 0.29 | 130 | 8.8 |
|  | dissolved | 0.90 | 160 | 9.0 |
|  | form) | 1.17 | 180 | 9.1 |
| 9 | Na-cilicate | 0.5 | 168 | 9.2 |
|  | (in dissolved | 1.0 | 231 | 9.7 |
|  | form) | 1.5 | 241 | 10.0 |

What is claimed:

1. A process for production of sorbents based on bentonite for the uptake of liquids wherein
   (a) homogenizing a poorly-swelling bentonite, wherein said bentonite has a water uptake capacity of less than 115% when measured in terms of dried bentonite, a residual water content of about 6 wt. %, a montmorillonite content of about 40–65 wt. %, and a water content of about 20–40 wt. % with a basic-reacting alkaline metal compound by thorough kneading to form a mixture and thus converting the poorly-swelling bentonite by ion exchange to a swelling bentonite, while the pH value of the mixture is not more than about 10.5,
   (b) gently drying the mixture, and
   (c) fragmenting the dried mixture.

2. The process of claim 1 wherein the bentonite has a water intake capacity of less than 115% when measured in terms of dried bentonite, a residual water content of about 6 wt. %, a montmorillonite content of about 50–60 wt. %, a water content of around 25–35 wt. % and wherein the pH value of the mixture is not more than about 10.0.

3. The process of claim 1 wherein the kneading is done with an energy consumption of about 1–10 kWh/ton of the kneaded mixture.

4. The process of claim 1 wherein the mixture during drying is exposed to not more than about 150° C. and the residual water content is adjusted to not less than about 6 wt. %.

5. The process of claim 1 wherein the bentonite is an alkaline earth bentonite which has a water uptake capacity of at least about 60% when measured in terms of dried bentonite, and a residual moisture content of about 6 wt. %.

6. The process of claim 1 wherein the bentonite is a calcium bentonite which has a water uptake capacity of at least about 60% when measured in terms of dried bentonite, and a residual moisture content of about 6 wt. %.

7. The process of claim 1 wherein the basic-reacting alkaline metal compound used is a water soluble sodium salt of a weak to medium strong acid.

8. The process of claim 7 wherein the basic-reacting alkaline metal compound used is a water soluble sodium salt of a weak to medium strong acid selected from the group consisting of carbonic acid, cilicic acid, oxalic acid, citric acid or acetic acid.

9. The process of claim 1 wherein the basic-reacting alkaline metal compound is used in a quantity of about 0.1–1.5% in terms of the bentonite.

10. The process of claim 1 wherein the basic-reacting alkaline metal compound is kneaded into the bentonite in the form of a solid.

11. The process of claim 1 wherein the basic-reacting alkaline metal compound is kneaded into the bentonite in the form of an aqueous solution.

12. The process of claim 1 wherein the dried mixture is processed to a grain size of about 0.1–10 mm.

13. A sorbent produced by the process of claim 1 wherein the water content of the sorbent is about 3–12 wt. %, the water uptake capacity is more than about 120 wt. % in terms of the dried bentonite with a residual water content of about 6 wt. %, and the pH value, measured in an 8% aqueous suspension, is about 7.5–10.5.

14. The sorbent of claim 13 wherein the mixture is blended with organic sorbents selected from the group comprising straw, sawdust, wood shavings, bark, porous synthetic beads, shredded paper, cellulose fibers, agricultural wastes, and polyacrylates to form a product mixture.

15. The sorbent of claim 13 wherein white pigments, disinfectants, or animal acceptance agents are added to the mixture.

16. A sorbent produced by the process of claim 1 wherein the water content of the sorbent is about 4–10 wt. %, the water uptake capacity is more than about 150% when measured in terms of the dried bentonite with a residual water content of about 6 wt. %, and the pH value, measured in an 8% aqueous suspension, is about 8.0–10.

17. The sorbent of claim 14 wherein the mixture is blended with organic sorbents selected from the group comprising straw, sawdust, wood shavings, bark, porous synthetic beads, shredded paper, cellulose fibers, agricultural wastes, and polyacrylates to form a product mixture.

18. The sorbent of claim 14 wherein white pigments, disinfectants, or animal excrement acceptance agents are added to the mixture.

* * * * *